United States Patent
Okrut et al.

(10) Patent No.: US 10,898,887 B2
(45) Date of Patent: Jan. 26, 2021

(54) SELECTIVE SOLID CATALYST FOR TAIL END OF OLEFIN-EPOXIDATION FLOW REACTOR

(71) Applicant: The Regents of the University of California, Oakland, CA (US)

(72) Inventors: Alexander Okrut, Oakland, CA (US); Alexander Katz, Richmond, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/326,872

(22) PCT Filed: Aug. 22, 2017

(86) PCT No.: PCT/US2017/047889
§ 371 (c)(1),
(2) Date: Feb. 20, 2019

(87) PCT Pub. No.: WO2018/039155
PCT Pub. Date: Mar. 1, 2018

(65) Prior Publication Data
US 2020/0009543 A1 Jan. 9, 2020

Related U.S. Application Data

(60) Provisional application No. 62/378,977, filed on Aug. 24, 2016.

(51) Int. Cl.
C07D 301/19 (2006.01)
B01J 29/89 (2006.01)
(Continued)

(52) U.S. Cl.
CPC .......... B01J 29/89 (2013.01); B01J 19/0053 (2013.01); B01J 35/02 (2013.01); C07D 301/19 (2013.01);
(Continued)

(58) Field of Classification Search
CPC .................. B01J 29/70; B01J 29/0308; B01J 2219/0004; B01J 21/16; B01J 2229/16;
(Continued)

(56) References Cited

U.S. PATENT DOCUMENTS 4,584,390 A 4/1986 Dieckelmann et al.
6,369,243 B1 4/2002 MacMillan et al.
(Continued)

FOREIGN PATENT DOCUMENTS

WO 2016050004 A1 4/2016

OTHER PUBLICATIONS

ISA/U.S. International Search Report and Written Opinion for PCT/US2017/047889; dated Oct. 24, 2017; 7 unnumbered pages.

*Primary Examiner* — Taylor V Oh

(57) ABSTRACT

In one example, a method for converting a first compound into a second compound is provided. The method includes providing the first compound in an entrance of a flow through reactor, wherein the entrance comprises a first catalyst and an oxidant, converting the first compound and the oxidant into the second compound as the first compound and the oxidant contact the first catalyst in the entrance of the flow through reactor while moving towards a tail end of the flow through reactor, and converting the first compound and the oxidant into the second compound via a solid catalyst comprising a white crystalline solid with a titanium content of about 0.5 to about 1.5 weight percent (wt %) in the tail end of the flow through reactor.

5 Claims, 9 Drawing Sheets

(51) Int. Cl.
  *B01J 19/00* (2006.01)
  *B01J 35/02* (2006.01)
(52) U.S. Cl.
  CPC ............... *B01J 2219/0004* (2013.01); *B01J 2219/00051* (2013.01); *B01J 2219/308* (2013.01); *B01J 2219/30207* (2013.01); *B01J 2219/30433* (2013.01); *B01J 2219/30475* (2013.01)
(58) Field of Classification Search
  CPC ............ B01J 2229/22; B01J 2229/34; B01J 2229/40; C07D 301/19
  USPC ...................................................... 549/523
  See application file for complete search history.

(56) References Cited

U.S. PATENT DOCUMENTS

| | | |
|---|---|---|
| 2004/0179983 A1 | 9/2004 | Balan |
| 2008/0031788 A1 | 2/2008 | Brophy et al. |
| 2011/0144361 A1 | 6/2011 | Berndt |
| 2016/0067694 A1 | 3/2016 | Ouyang et al. |
| 2017/0226429 A1* | 8/2017 | Shi ................... B01D 53/0423 |

* cited by examiner

SELECTIVE SOLID CATALYST FOR TAIL END OF OLEFIN-EPOXIDATION FLOW REACTOR

CROSS REFERENCE TO RELATED APPLICATIONS

This application claims priority to U.S. Provisional Patent Application Ser. No. 62/378,977, filed Aug. 24, 2016, which is herein incorporated by reference in its entirety.

REFERENCE TO GOVERNMENT FUNDING

This invention was made with Government support under Grant No. IIP1542974, awarded by the National Science Foundation (NSF). The Government has certain rights in the invention.

FIELD OF THE INVENTION

The present disclosure relates generally to a crystalline solid catalyst used for flow reactors.

BACKGROUND

Propylene oxide (PO) is an industrial commodity chemical for polyurethanes, polyols, surfactants, and lubricants with a growing current global production of capacity of more than $8·10^6$ metric tons per year. Nearly 50% of worldwide PO production uses organic hydroperoxide to oxidize the double bond of propylene to generate propylene oxide, and, in this approach, for each generated PO, an organic alcohol co-product is synthesized, sometimes (depending on economics) being as valuable or even more valuable than the PO itself. The most commonly used organic hydroperoxides for PO synthesis are tert-butyl hydroperoxide (TBHP), ethylbenzene hydroperoxide (EBHP) and cumene hydroperoxide. The methyl tert-butyl ether (MTBE) route is typically catalyzed by a soluble molybdenum naphthenate salt. Both the cumene and ethylbenzene hydroperoxide routes use a solid rather than soluble epoxidation catalyst for PO production, consisting of supported Ti Lewis-acid sites on amorphous mesoporous silica.

For safety reasons, as well as avoidance of by-product formation in the separation train, it is important to convert over 99% of the organic hydroperoxide in the tail end of the PO synthesis flow reactor. These high conversions lead to catalyst active-site inhibition by both the epoxide product as well as the alcohol co-product. When combined with the low organic hydroperoxide concentration under tail-end conditions, this leads to sluggishness in rate for all currently used catalysts. This sluggishness in turn requires higher temperatures (sometimes in excess of 60° C. compared to entrance) in the tail end of the PO synthesis reactor, which leads to greater energy consumption, costs, and waste due to reduced catalyst selectivity in the tail end, and contributes to catalyst deactivation.

SUMMARY

According to aspects illustrated herein, there is provided a method for converting a first compound into a second compound. One disclosed feature of the embodiments is a method comprising providing the first compound in an entrance of a flow through reactor, wherein the entrance comprises a first catalyst and an oxidant, converting the first compound and the oxidant into the second compound as the first compound and the oxidant contact the first catalyst in the entrance of the flow through reactor while moving towards a tail end of the flow through reactor, and converting the first compound and the oxidant into the second compound via a solid catalyst comprising a white crystalline solid with a titanium content of about 0.5 to about 1.5 weight percent (wt %) in the tail end of the flow through reactor.

In another aspect, the present disclosure provides a reactor. The reactor includes an entrance comprising a first catalyst to convert a first compound into a second compound using an oxidant and a tail end comprising a second catalyst that is different from the first catalyst, wherein the second catalyst comprises a white crystalline solid with a titanium content of about 0.5 to about 1.5 weight percent (wt %) to convert the oxidant into the second compound.

BRIEF DESCRIPTION OF THE DRAWINGS

The teaching of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
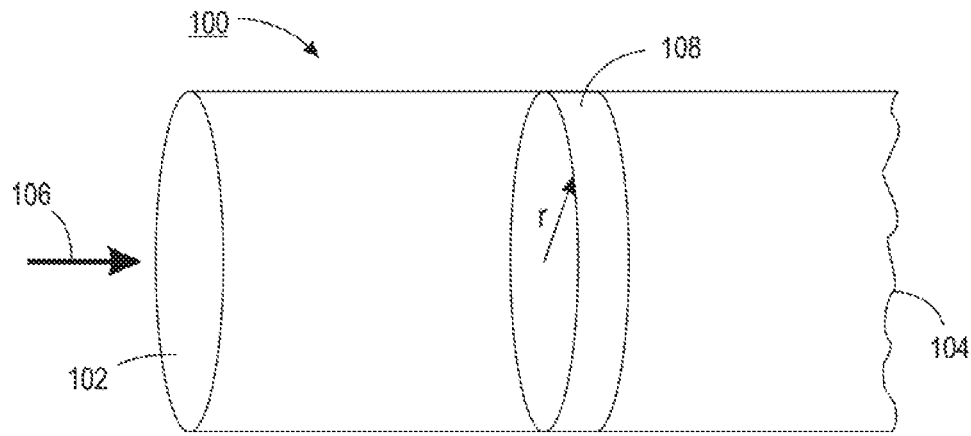
FIG. 1 illustrates one embodiment of an example flow reactor.

The present disclosure provides a crystalline solid catalyst for olefin epoxidation is described, which is highly selective for epoxide production at the extreme conditions of high temperature and organic-hydroperoxide conversion that correspond to the tail end of the olefin-epoxidation reactor. This catalyst can be used at the tail end of the reactor, in conjunction with other catalysts earlier in the flow reactor, thus resulting in at least two separate catalysts; one or more for the entrance and middle, and another for the tail end of the reactor.

Solid catalysts comprising titanium grafted on an amorphous silica support are useful for the preparation of epoxides using olefin and organic hydroperoxide as oxidant. A relevant example is WO2007/128666, which describes the preparation of such a heterogeneous titanium catalyst. Besides heterogeneous catalysts, homogeneous catalysts, such as molybdenum naphthenate are also useful for the preparation of epoxide (see U.S. Pat. No. 3,351,635).

Both of these prior-art catalysts are useful at the conditions of the entrance of a reactor, where the organic-hydroperoxide conversion is low, along with the temperature, and a key aspect of the catalyst is its productivity and activity. A typical flow through reactor may include an entrance and a tail end, or exit portion, which operate under extremely different conditions.

As discussed above, at the tail end of the reactor, comprising conversions of organic-hydroperoxide above 80%, preferably above 85% and most preferably above 90%, compared with 0% at the entrance to the reactor, there is excess alcohol coproduct as well as a high concentration of epoxide relative to hydroperoxide. Indeed, the purpose of the tail-end of the reactor is to react away remaining organic hydroperoxide before the separation workup.

Typical conversions after the end of the tail end of the reactor exceed 99% and preferably exceed 99.5%, and most preferably exceed 99.7%. To avoid waste and increase profitability, high selectivity to epoxide product is desired throughout the reactor. Selectivity is defined as a fraction of organic hydroperoxide consumed that is converted to epoxide. The selectivity is desired to be as high as possible and is typically above 95% when calculated over the entire olefin-epoxidation reactor. However, at the tail end of the reactor, the aforementioned and known prior-art catalysts are sluggish and operate suboptimally with respect to their ability to selectively convert remaining organic hydroperoxide to desired epoxide product.

Some catalysts are sufficiently reactive and selective at the start of the reaction. Examples of some catalysts that can be used for the conversion are listed in U.S. Patent Application Publication Number 2016/0067694 (hereinafter the '694 Publication), which is incorporated by reference in its entirety. However, with progressing conversion of the organic hydroperoxide, the ability of some catalysts to catalyze the desired epoxidation reaction becomes sluggish as a result of several factors.

One factor is a predominant amount of alcohol coproduct and epoxide act as catalyst poisons that slow down the rate of conversion and decrease selectivity. As a result, temperatures above 110° C., preferably above 120° C., and most preferably above 130° C. are required to achieve the required high conversion of the organic hydroperoxide in the tail end of the reactor. At these temperatures, the currently used catalysts are less selective, i.e., while organic hydroperoxide is being consumed, less propylene oxide is formed. What is needed is a catalyst that can achieve higher selectivity to epoxide specifically under the extreme conditions of high temperature and compositions corresponding to high organic-hydroperoxide conversion—both of which correspond to the tail end of the reactor.

Thus, to improve the PO synthesis process based on an organic hydroperoxide oxidant, there is a need to reduce the deactivation of the catalyst, while maintaining high selectivity by minimizing synthesis of undesired by-products. Therefore another, more stable and more selective epoxidation catalyst compared with those currently used in industrial production is needed.

FIG. 1 illustrates a flow through reactor 100 of the present disclosure. The flow through reactor 100 may have an entrance 102 and a tail end, or exit, 104. The flow through reactor 100 may have a middle segment 108. The flow through reactor 100 may be sized to have a radius "r" for a particular flow rate, production rate, scale, and the like.

The entrance 102 may include a first catalyst, the tail end 104 may include a second catalyst, and the middle segment 108 may include a mix of the first catalyst and the second catalyst. The middle segment 108 may have a gradient mixture of the first catalyst and the second catalyst (e.g., more of the first catalyst towards and entrance 102, a 50/50 mixture in a center, more of the second catalyst towards the tail end 104).

In one embodiment, the second catalyst may be a preferential catalyst for the tail end 104 of the flow through reactor 100 which operates under more extreme conditions of temperature (e.g., temperatures of approximately 110 degrees Celsius (° C.) and above) and presence of catalyst poisons, such as epoxide and alcohol coproduct, relative to the entrance 102 where the temperature is low (e.g., approximately 40° C.) and these poisons are largely absent. In one embodiment, a first compound (e.g., an olefin) with an oxidant (e.g., hydroperoxide) may be provided in an axial flow direction, illustrated by an arrow 106, through the first catalyst in the entrance 102. The first compound may be converted into a second compound (e.g., an epoxide) plus one or more catalyst poisons (e.g., alcohol) as the first compound flows through the flow through reactor 100 along the axial flow direction 106. In other words, the conversion of the oxidant, the alcohol and epoxide concentration, and the temperature may increase across the flow through reactor 100 moving from the left to the right of FIG. 1. The oxidant may be converted in the tail end 104 via a second catalyst (e.g., the preferential catalyst of the present disclosure).

The preferential, or second, catalyst of the present disclosure may comprise a solid catalyst that can achieve higher selectivity to epoxide. The solid catalyst may achieve higher selectivity under the extreme conditions of high temperature and organic-hydroperoxide conversion that correspond to the tail end 104 of the flow through reactor 100.

In one embodiment, multiple catalysts may be used in a single reactor 100. In one embodiment, the second catalyst of the present disclosure is used as the preferential catalyst at the tail end 104 of the flow through reactor 100 in the form of a packed bed. In addition, one or more other first catalyst(s) are used at the entrance 102 of the flow through reactor 100.

Figure 3:
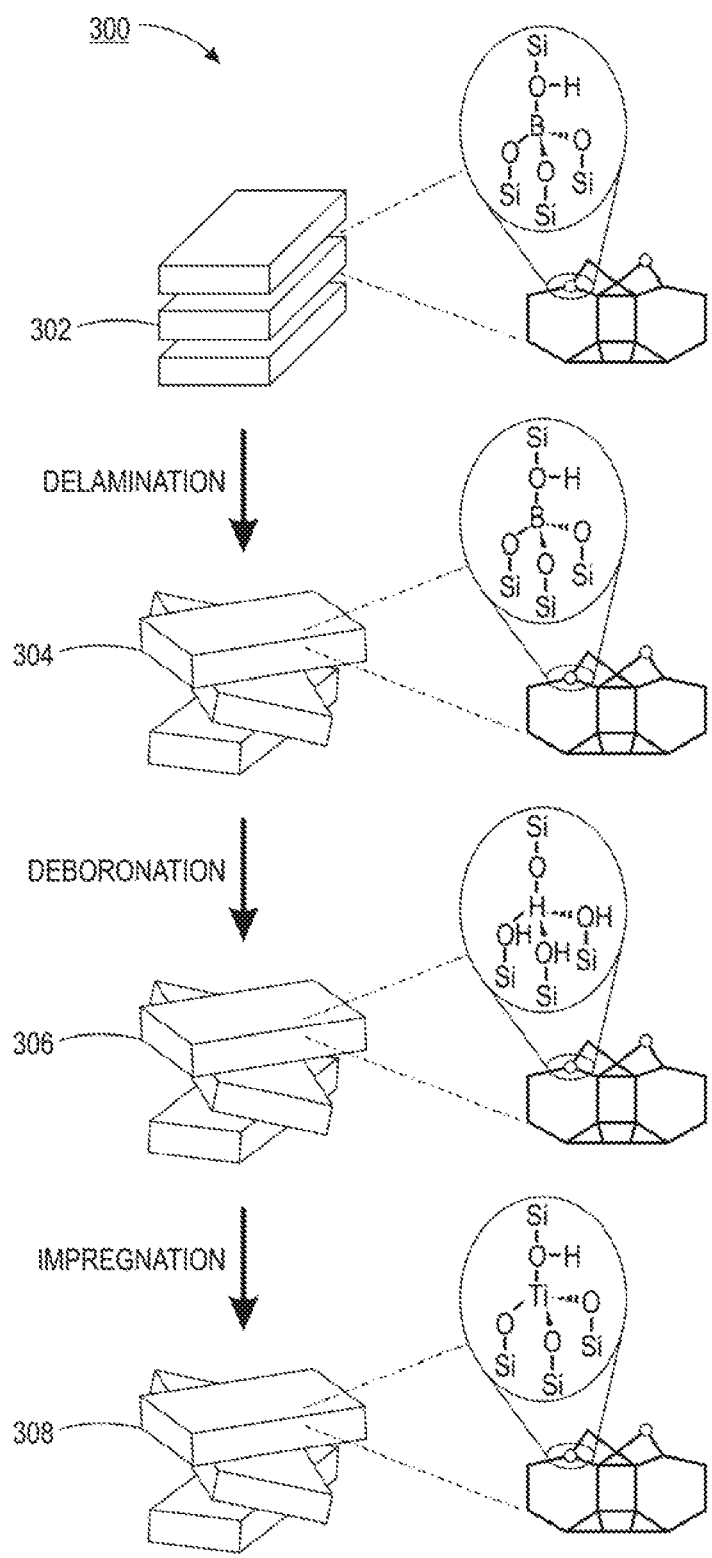
FIG. 3 illustrates an example process flow for synthesizing a catalyst of the present disclosure.

The second catalyst of the present disclosure may be a heterogeneous catalyst that is a white crystalline solid with a titanium content of about 0.5 to about 1.5 wt %, which is based on a layered zeolite precursor. More specifically, the catalyst of the present disclosure is synthesized by the delamination of the layered zeolite precursor followed by titanium insertion. An example of the synthesis of the second catalysts is illustrated in FIG. 3 and discussed below.

A related synthesis has been described by (Ouyang et al., *Dalton Trans.* 2014, 43, 10417-10429). An example of the catalyst is Ti-UCB-4 provided in the '694 publication. Although the '694 publication illustrates a variety of different catalysts used in certain conditions, none of the conditions in the '694 publication include the extremely high temperatures in the tail end 104 of a flow-through reactor 100 and the presence of catalysts poisons, as described herein.

As the examples demonstrate below, the present disclosure demonstrates that this catalyst can be used to convert a terminal olefin to the corresponding 1,2 epoxyalkane using an organic hydroperoxide selectively, at the extreme conditions corresponding to the tail end of the reactor (e.g., temperatures as high as 130° C. and the presence of catalyst poisons such as epoxides and alcohol). The present disclosure also demonstrates a configuration in which this catalyst can be used with existing catalysts to improve the selectivity at the tail-end 104 of the flow through reactor 100, using a packed bed of the catalyst of the present disclosure, in conjunction with one or more other catalyst(s) elsewhere before (i.e. at lower residence times and lower organic-hydroperoxide conversions) in the olefin-epoxidation flow reactor.

Figure 2:
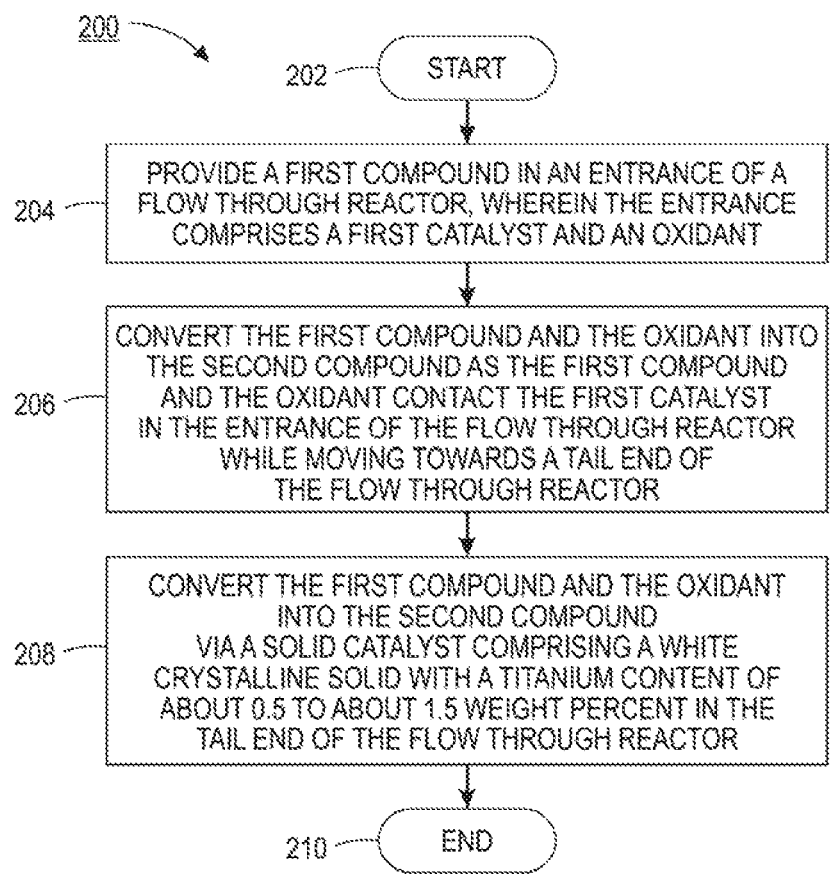
FIG. 2 illustrates a flow chart of an example method for converting a first compound into a second compound.

FIG. 2 illustrates a flow chart of an example method 200 for converting a first compound into a second compound. The method 200 may be performed in the flow through reactor 100 illustrated in FIG. 1 and discussed above.

At block 202, the method 200 begins. At block 204, the method 200 provides a first compound in an entrance of a flow through reactor, wherein the entrance comprises a first catalyst and an oxidant. In one embodiment, the first compound may be an olefin. The first catalyst may be a solid catalyst or a dissolved homogenous catalyst. In one embodiment, an example of a solid catalyst may include titanium grafted on an amorphous silica support. An example of the homogenous catalyst may be molybdenum napthenate. In one embodiment, the oxidant may be organic hydroperoxide.

At block 206, the method 200 converts the first compound and the oxidant into a second compound as the first compound and the oxidant contact the first catalyst in the entrance of the flow through reactor while moving towards a tail end of the flow through reactor. For example, the first compound may be converted into the second compound and one or more catalyst poisons.

At block 208, the method 200 converts the first compound and the oxidant into the second compound via a solid catalyst comprising a white crystalline solid with a titanium content of about 0.5 to about 1.5 weight percent in the tail end of the flow through reactor. The solid catalyst of the present disclosure used in the extreme conditions of the tail end of the flow through reactor provide high conversion of the oxidant before the second compound is removed. As noted above, the catalyst poisons that are produced during the conversion of the first compound may retard the ability of the first catalyst to convert the oxidant. However, the solid catalyst of the present disclosure used in the extreme conditions of the tail end of the flow through reactor provide conversions of over 99% of the oxidant. At block 210, the method 200 ends.

FIG. 3 illustrates an example process flow 300 for synthesizing the second catalyst used in the tail end of a flow through reactor of the present disclosure. At block 302, a layered zeolite catalyst precursor is provided. The layered zeolite catalyst may be B-SSZ-70. Calcination of the B-SSZ-70 synthesizes the three-dimensional zeolite B-SSZ-70. The crystalline lattice of B-SSZ-70 is well defined with boron atoms located in framework T-sites.

At block 304, the zeolite catalyst is delaminated. The ordered crystalline framework structure of the layered zeolite catalyst precursor is delaminated at the precursor stage by treating with a surfactant followed by subsequent breaking of intersheet covalent Si—O—Si and Si—O—B connectivity between layers to affect layer exfoliation, thereby resulting in delaminated zeolite B-UCB-4. The typical increase in the external surface area is approximately a factor of 2 greater for the delaminated zeolite over its three-dimensional calcined counterpart (i.e. zeolite without delamination).

The delaminated-zeolite catalyst circumvents the typical steric limitations imposed by zeolitic microporous frameworks, which form the basis for zeolite shape selectivity and three-dimensional confinement effects in catalysis, as delamination increases the available exposed external surface area. The delaminated UCB-4 support material may be synthesized from the crystalline molecular sieve B-SSZ-70.

At block 306, delaminated-zeolite catalyst is deboronated. For example, the boron atoms occupying framework positions in B-UCB-4 are removed via aqueous acid treatment. The resulting deboronated UCB-4 framework consists of silanol nests, which are subsequently reoccupied by framework titanium atoms.

At block 308, the deboronated zeolite catalyst is impregnated with titanium (Ti) atoms. As noted above, the silanol nests are reoccupied by a framework of titanium atoms via treatment with titanium n-butoxide. The obtained Ti-UCB-4, therefore, represents a crystalline 2D analogue of the molecular sieve, with a higher external surface area and accessible framework Ti sites.

While most of the Ti atoms in Ti-UCB-4 are expected to be located in the framework, where they are coordinated to four framework oxygen atoms, it is also expected to be some Ti still grafted to isolated external-surface silanols (i.e. not within a silanol nest). Based on the known structure of related MCM-22 zeolite (which like SSZ-70 also consists of a layered-zeolite precursor consisting of 12-membered-ring cups), these sites are anticipated to be a minority, and the majority should consist of Ti coordinated to silanol nests. These nests offer improvement in the stability of the second catalyst used in the tail end of the flow-through reactor, as a result of chelation of multiple framework oxygens to the Ti site. However, in addition, the nests can also offer improved selectivity due to confinement within the nest site.

EXAMPLE 1

The focus of Example 1 was on investigating and quantifying catalyst deactivation and selectivity for a model surrogate of the styrene monomer & propylene oxide (SMPO) process, comprising of epoxidation of terminal olefin 1-octene with ethylbenzene hydroperoxide as the organic hydroperoxide, with time on stream in a flow reactor. This olefin choice obviates higher pressures that would otherwise be required in order to maintain a liquid phase in the flow reactor if using propylene instead as the olefin. The two expected products of this reaction are 1,2-epoxyoctane and 1-phenylethanol. A loss in selectivity results from consuming organic hydroperoxide (the limiting reagent) in a manner that does not lead to the synthesis of an epoxide product (e.g., decomposition of organic hydroperoxide to dioxygen and alcohol coproduct). This loss of selectivity would lead to other, undesirable, organic-hydroperoxide decomposition products such as $O_2$ and acetophenone (oxidized alcohol to ketone), and has been already identified as a significant problem for PO synthesis via organic hydroperoxides, including the SMPO process, as discussed above.

For Example 1, liquid samples from catalysis were analysed using an Agilent gas chromatography (GC) system consisting of a GC 6890A plus with helium as the make-up gas, air as the utility gas and a high-resolution capillary column with 50.0 m length, 320 μm diameter and 1.05 μm in film thickness. The gas chromatograph is equipped with a flame ionization detector (FID). The temperature program runs from 80-180° C. Powder X-ray diffraction (PXRD) patterns were measured using a Bruker GADDS D-8 diffractometer and Cu-Kα radiation. Data were collected in the 2θ range from 3° to 30° with a step size of 0.02° and a dwell time of 2 seconds (s). PXRD peaks at 2θ values of lower than 5° are not discussed due to instrument limitations. Ultraviolet-visible spectroscopy (UV Vis) for solid materials was performed on a Cary 400 spectrophotometer (Varian). Samples were measured with an average time of 0.166 s and a wavelength data interval of 0.5 nanometers (nm), resulting in a scan rate of 180.7 nm/minute (min). The results are corrected by measuring a baseline of polytetrafluoroethylene and reflectance data were converted into Kubelka-Munk pseudoabsorbance units. The determination of the Ti contents of materials was performed via liquid-phase UV-Vis spectroscopy via the following procedure: 20 mg catalyst were mixed with 1 mL pure H2SO4 in a 10-mL volumetric flask and left for 1 h. Then, a few drops of water and 0.11 mL of 30% H2O2 solution were added. The volumetric flask was filled with water to the 10 mL mark. The concentration of titanium in the prepared solution was calculated from the value of absorbance at 408 nm in the UV-Vis spectrum using a calibration curve. Micropore volume, external surface area, and total pore volume of solid samples were measured via Nitrogen physisorption at 77K using an ASAP 2020 Accelerated Surface Area and Porosimetry system (Micromeritics). About 100 mg sample were weighed and degassed under vacuum at 250° C. for 4 hours. The analysis gas was nitrogen which was adsorbed at a temperature of −195.8° C. The equilibration interval was 45 seconds. The resulting data were calculated by the ASAP 2020 software.

Titanium Grafting—SiO$_2$ (Selecto silica gel, particles size 32-63 μm) and UCB-4 were calcined at 550° C. for 10 hours. Then, 1 g of each material was dried in a 15.0 mL high-pressure flask at 120° C. for at least 3 hours. Under a stream of argon, 10.0 mL of anhydrous 1-butanol and 1 mL of Titanium(IV)-n-butoxide were added. The mixture was stirred at 135° C. for 1 hour. After cooling to room temperature, the white solid products were filtered and washed with 1-butanol. After drying at 120° C., the white powders were crushed with a pestle and calcined at 550° C. for 10 hours. By UV-Vis spectrometry, typical Ti contents of 0.41-0.43 wt % for the Ti-UCB-4 and 1.38-1.67 wt % for Ti—SiO$_2$ were determined.

Catalysis in a flow reactor—In a typical experiment, Ti-UCB-4 was pelletized to a particle size of 180-250 μm. Then 18-50 mg of calcined catalyst were packed into a stainless-steel reactor (L=41 mm, ø=6 mm) between layers of glass wool. Layers of glass beads before and after the catalyst layer were used to stabilize the catalyst bed in the middle of the reactor and to enable thorough mixing of the reaction solution. A typical stock solution consists of 1029.0 mmol (115.5 g) of 1-octene, 32.1 mmol (4.4 g) of EBHP, 62.4 mmol (8.7 g) of ethylbenzene, 188.4 mmol (24.2 g) of 1,2-epoxyoctane, 2.7 mmol (1.5 g) of acetophenone, 186.6 mmol (22.8 g) of 1-phenylethanol and 11.9 mmol (1.5 g) of n-nonane as an internal standard. The packed reactor was heated under vacuum at 140° C. for at least 4 hours. After cooling to room temperature, the reactor was flushed with 1-octene and connected to a syringe that contained the reaction solution. The required flow rate was controlled using a syringe pump. The reactor was submerged in an oil-bath, which was held at a temperature of 110° C. Samples were collected for 1 hour over different periods of time during the experiment. In order to allow the system to equilibrate, sample collection started at least 2 h after the experiments began. The samples were analyzed via gas chromatography using n-nonane as internal standard.

For practical reasons, two separate experiments were conducted to obtain data for the range of 1-24 hours: first, an experiment over 12 hours was performed and then, an experiment over 24 hours was performed. During the 24-hour experiment, the second range of 12 hours of the experiment were measured. For the experiments using Ti-UCB-4, the illustrated graph is an average of multiple similar experiments (including reproductions). A general observation is the broad scattering of the selectivity values of EBHP for 1,2 epoxyoctane. This is caused by the deviation when measuring the relatively small signal change during 1,2-epoxyoctane formation, which is divided by the relatively large signal change during EBHP consumption. Error bars were calculated based on the standard deviation. Manually added trend lines to guide the eye show the average selectivity and a decreasing trend for the conversion of EBHP in some ranges. For the run with the highest EBHP conversion >90%, the flow rate was lowered after 12 hours to increase and set the conversion.

Batch-reactor testing of catalyst recyclability—5.0 mg of calcined catalyst were dried in a vial at 120° C. for at least 4 hours. After cooling to room temperature, 2.5 mL of stock solution were added and the mixture was stirred at 110° C. for a selected time and cooled down to take a sample. After sampling, the mixture was stirred again at 110° C. and after a certain time a second and third sample were taken in the same way as before. The samples were analyzed by gas chromatography using n-nonane as internal standard. A typical stock solution consists of 6.830 mmol (0.765 g) of 1-octene, 0.268 mmol (0.037 g) of EBHP, 12.915 mmol (1.369 g) of ethylbenzene, 1.061 mmol (0.136 g) of 1,2-epoxyoctane, 0.216 mmol (0.026 g) of acetophenone, 1.195 mmol (0.146 g) of 1-phenylethanol and 0.203 mmol (0.026 g) of n-nonane as an internal standard. This experiment was performed with fresh Ti—SiO$_2$ and Ti-UCB-4, and also with spent Ti—SiO$_2$ and Ti-UCB-4, which were already used for at least 50 hours in a flow test and afterwards calcined at 550° C. for 10 h.

Results—Support materials consisting of calcined B-SSZ-70, UCB-4, and amorphous SiO$_2$ were structurally characterized by PXRD prior to Ti incorporation. Characteristic peaks in the powder pattern at 2θ values of 7.2°, 14.5°, and 26.3° are consistent with previously reported data for calcined SSZ-70. The powder pattern corresponding to calcined UCB-4 consists of similar Bragg peaks. This provides support for intact crystallinity of this material following delamination and calcination, since UCB-4 is synthesized from the B-SSZ-70 layered zeolite precursor. Peaks at 7.9° and 10.0° 2θ for UCB-4 are broader and less intense for the delaminated material UCB-4 compared to the starting material B-SSZ-70. The peaks indicate a greater disorder with respect to the z-axis orientation after delamination. Such a result is expected for successful delamination based on the resulting random z-orientation of sheets. This is a desirable outcome as it is consistent with exposing more external surface for Ti insertion during grafting to silanol nests as well as greater densities of active sites (i.e. only those sites on the external surface are active) during epoxidation reaction. The lack of any observed Bragg peaks for amorphous silica is consistent with the lack of long-range order in this material.

The same materials were also characterized via N$_2$ physisorption at 77K, to evaluate porosity and external surface area, which is the relevant surface area for Ti incorporation and to the catalysis investigated here, as a result of the steric bulk of the reagents involved. Resulting data consists of the N$_2$ adsorption/desorption isotherms as a function of relative pressure for the three materials, and Table 1 below, summarizes the micropore and mesopore volumes as well as the external surface areas determined by the t-plot method from these data. There are significant differences between all isotherms. The low-pressure uptakes within the isotherms correspond to micropores, and the micropore volume for the calcined B-SSZ-70 is 0.17 mL/g, whereas for UCB-4, it is less—at 0.15 mL/g. This decrease in micropore volume is consistent with loss of that microporosity that would otherwise reside in between layers. The amorphous $SiO_2$ support, however, shows nearly no micropore volume, as typical for mesoporous silica materials.

TABLE 1

Characteristics for the supporting materials used.

| Material | Micropore volume [mL/g]$^a$ | External surface area [m$^2$/g]$^a$ | Total pore volume [mL/g]$^a$ | Ti-content [wt %] |
|---|---|---|---|---|
| B-SSZ-70 | 0.17 | 74 | 0.35 | N/A |
| Ti—SiO$_2$ | 0 | 506 | 0.71 | 1.52 ± 0.15 |
| Ti-UCB-4 | 0.15 | 113 | 0.43 | 0.42 ± 0.01 |

Using the t-plot method, the external surface area was calculated. There is a clear increase of external surface area for UCB-4 as synthesized from B-SSZ-70. This external surface area of B-SSZ-70 is 74 m$^2$/g, considerably less than the 113 m$^2$/g calculated for UCB-4. Amorphous $SiO_2$ has a much higher external surface area of 506 m$^2$/g using the same approach—and the similarity of this value to the BET surface area (BET surface area of 402 m$^2$/g) suggests that most if not all of the internal mesopores of $SiO_2$ are unconfined and appear like external surface area in a t-plot calculation. The value of the total pore volume at a P/Po of near unity represents the total pore volume. This is also observed to increase as a result of delamination, when comparing calcined B-SSZ-70 (0.35 mL/g) and UCB-4 (0.43 mL/g) materials, with amorphous $SiO_2$ having a much higher total pore volume of 0.71 mL/g and exhibiting hysteresis within the isotherm, as characteristic for a mesoporous material. In summary, delamination of B-SSZ-70 preserves crucial aspects of crystallinity when synthesizing UCB-4 while increasing the external surface area and total pore volume. Notwithstanding, the support material with the highest external surface area and total pore volume is represented by amorphous silica.

Following Ti incorporation, solid-state diffuse-reflectance UV-Vis spectroscopy between 200 nm and 500 nm allows investigation of the nature of Ti sites within the materials. The UV-Vis spectrum of Ti-UCB-4 consists of one major band spanning 200 nm-328 nm, with a maximum at 210 nm. A band at 210 nm is assigned in related crystalline zeolitic Ti—$SiO_2$ catalysts to correspond to isolated Ti(SiO)$_4$ or Ti(OSi)$_3$OH framework sites. Based on this, we infer that Ti-UCB-4 comprises isolated Ti framework sites. A slight shoulder around 260 nm indicates presence of titanium sites in non-framework positions, such as those grafted on external-surface isolated silanols. In comparison, the UV-Vis spectrum of amorphous Ti—$SiO_2$ shows a broad band spanning between 200 nm and 350 nm, with a peak maximum at 278 nm and a shoulder at approximately 247 nm. The data show that the vast majority of Ti sites in amorphous Ti—$SiO_2$ are isolated surface-grafted sites, represented by the shoulder at 247 nm. In addition, the band around 260 nm and higher wavelength indicates formation of titanium oxide oligomers, which may form during calcination. No bulk anatase formation is observed. In summary, the preponderance of framework Ti sites in Ti-UCB-4 versus the grafted surface sites of amorphous Ti—$SiO_2$ suggests both materials to be good candidates for testing the central hypothesis of this manuscript, as it relates to effect of amorphous versus crystalline support environment on Ti-site catalysis.

Tail-end epoxidation catalysis in a flow reactor—The crystalline Ti-UCB-4 and amorphous Ti—$SiO_2$ were compared as olefin epoxidation catalysts for the epoxidation of 1-octene with EBHP in a flow reactor, under tail-end conditions. Tail-end conditions correspond to a feed at the entrance of the flow reactor, which represents 80% conversion of a hypothetical entrance-to-reactor feed stream consisting of EBHP and olefin only (i.e. negligible epoxide and alcohol coproduct). That is to say, the flow reactor is fed an amount of epoxide and alcohol that is in large excess relative to EBHP, such that it would appear to correspond to 80% EBHP conversion of a hypothetical entrance-to-reactor feed consisting of EBHP and olefin only. The conversion discussed below refers to a zero conversion basis at the entrance of our flow reactor (i.e., conversion is defined to be that conversion that is actually achieved within the flow reactor, with the tail-end feed as inlet to the reactor corresponding to 0% conversion within the reactor). Flow reactor conditions were otherwise as described above in Example 1.

Figure 9:
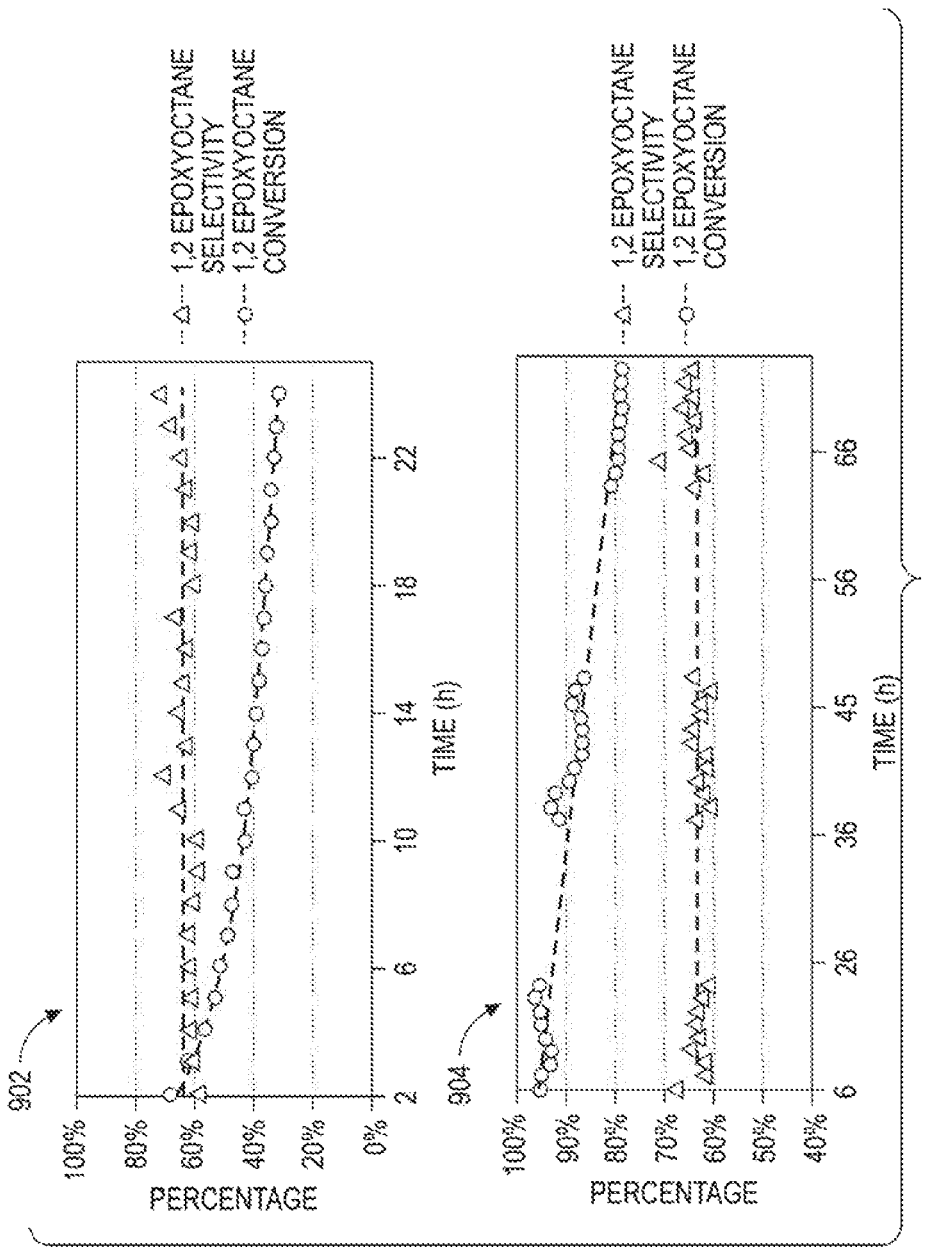
FIG. 9 illustrates charts of EBHP conversion and epoxide selectivity data of a Ti—$SiO_2$ catalyst in a flow through reactor.
Figure 10:
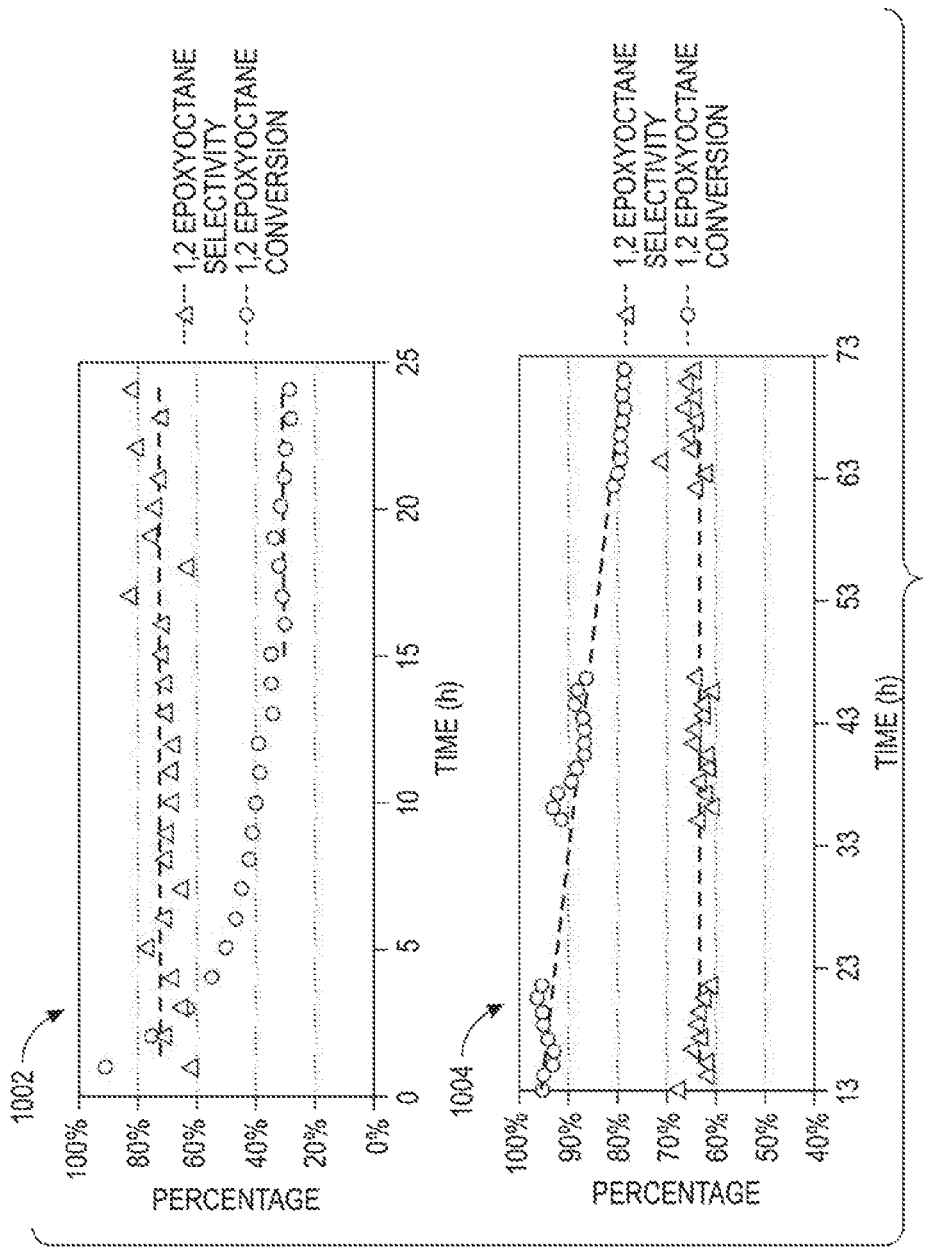
FIG. 10 illustrates charts of EBHP conversion and epoxide selectivity data of a Ti-UCB-4 catalyst in a flow through reactor.

The Ti—$SiO_2$ catalyst was first tested at a low target EBHP conversion of <35% for a period of 24 hours. The EBHP conversion and selectivity for 1,2-epoxyoctane for the amorphous Ti—$SiO_2$ catalyst are illustrated in FIG. 9. Graph 902 illustrates a lowest conversion of 1,2-epoxyoctane and graph 904 illustrates a highest conversion of 1,2-epoxyoctane. As shown in the chart 902, the Ti—$SiO_2$ achieves an initial EBHP conversion of 67%, which continuously decreases over a 24-hour period, down to a value of 31%. The selectivity for 1,2-epoxyoctane remained relatively constant over this 24-hour period, averaging 63±3% as shown in the graph 902. In comparison, under similar conditions, the EBHP conversion for the crystalline Ti-UCB-4 catalyst initially decreases at low time on stream and then remains constant after 15 h until the end of the experiment. This data is shown in chart 1002 of FIG. 10. FIG. 10 illustrates the EBHP conversion and selectivity for 1,2-epoxyoctane in the crystalline Ti-UCB-4 catalyst at a lowest conversion in the chart 1002 and at a highest conversion in chart 1004. The selectivity of EBHP for 1,2-epoxyoctane remains constant for Ti-UCB-4 over the entire 24 hour period and averages 73±4%, as shown in the chart 1002.

Next, a target EBHP conversion of greater than 90% was achieved in flow experiments that were run continuously for 72 hours using Ti—$SiO_2$ as catalyst. For the Ti—$SiO_2$ catalyst, the EBHP conversion starts at 95%, and continuously drops to 78% during the run, as shown in chart 904 of FIG. 9. While there is some slight fluctuation observed in the EBHP conversion versus time on stream, the overall trend clearly represents a decrease in the EBHP conversion with increasing time on stream, indicating a deactivating Ti—$SiO_2$ catalyst, with no evidence for a steady state even after 63 h of time on stream for this catalyst. The selectivity of the Ti—$SiO_2$ catalyst remains stable around 64±2%, as shown in the chart 904 of FIG. 9. In contrast, under similar conditions, data for Ti-UCB-4 is illustrated in the chart 1004 of FIG. 10. As shown in the chart 1004, the Ti-UCB-4 crystalline catalyst exhibits no clearly observable drop in activity after 37 hours time on stream, demonstrating a clear steady state performance after 24 h time on stream, without continuing deactivation during the run, at an EBHP conversion of 92%. This EBHP conversion represents only a slight drop in the 99% conversion observed at initial time on stream. The selectivity for the Ti-UCB-4 catalyst also remained stable upon increasing time on stream, and averaged at 73±4%, as shown in the chart 1004 of FIG. 10. Altogether, the experiments demonstrate that the EBHP conversion decreases much more significantly for Ti—SiO$_2$ nificantly higher than that for Ti—SiO$_2$ of 9.6·10$^3$ mL/(h·g Ti). This analysis demonstrates the clear benefit of the crystalline material Ti-UCB-4 over the amorphous material Ti—SiO$_2$ on a per Ti active-site basis.

TABLE 2

OVEVIEW OF STUDIED CATALYSTS

| Material | Crystalline | Conversion reaches steady-state[1] | Average selectivity | Stable selectivity | Ti-sites in framework | Visual color of spent catalyst | Reaction rate constant k' mass-based [mL/h · g] | Reaction rate constant k titanium content-based [mL/h · g] |
|---|---|---|---|---|---|---|---|---|
| Ti—SiO$_2$ | no | no | 64% (±0%) | yes | no | orange | 132 | 9.6 · 10$^3$ |
| Ti-UCB-4 | Yes | yes | 73% (±1%) | yes | yes | light yellow | 103 | 25.0 · 10$^3$ | relative to Ti-UCB-4 as catalyst, during 1-octene epoxidation catalysis in a flow reactor. In particular, during a period of 72 hours, the amorphous Ti—SiO$_2$ catalyst deactivates continuously, whereas the crystalline Ti-UCB-4 shows no evidence of deactivation after reaching a steady state operating level after 24 h time on stream. A hypothesis for the observed initial decrease (especially during the first 15 h time on stream) of the conversion in both catalysts involves the built up of polymer/organic matter, which can block the Ti active sites. This observed stability of Ti-UCB-4 relative to Ti—SiO$_2$ can be rationalized on the basis of Ti sites in the former not being as accessible to polymer/organic contaminants. This may be a consequence of their location within less accessible (to polymer) nest sites.

Figure 11:
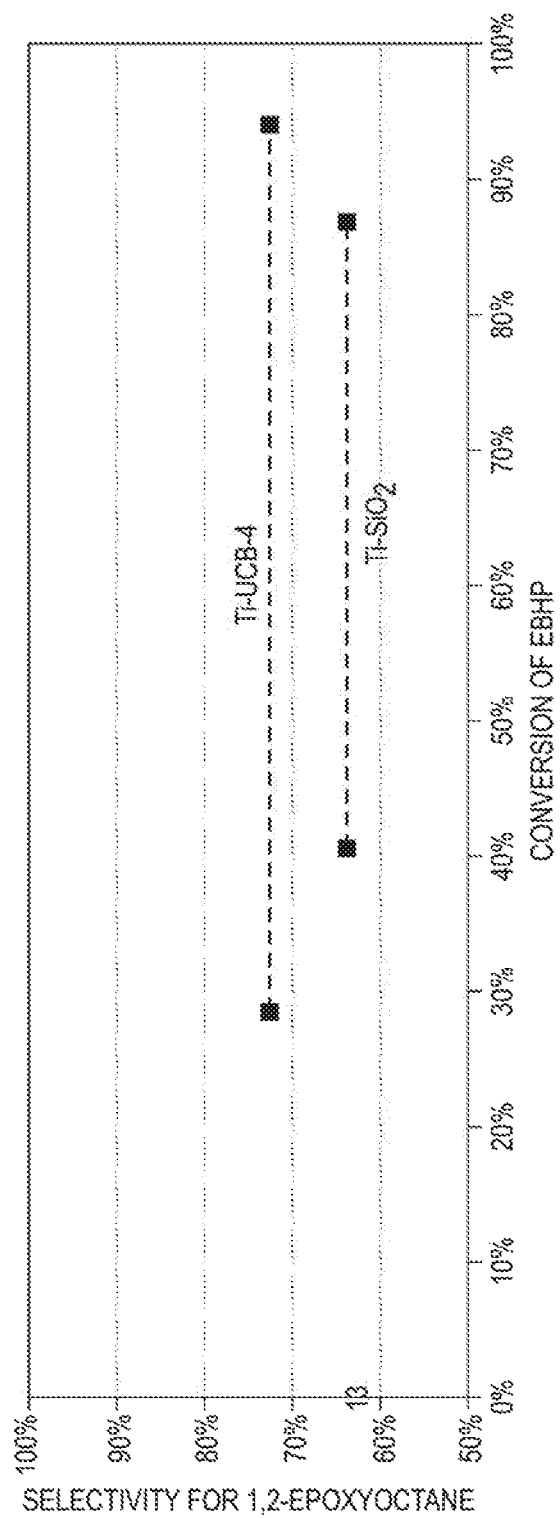
FIG. 11 illustrates a chart that summarizes the EBHP conversion and epoxide selectivity data of different catalysts in a flow through reactor.

Experiments in two different regions of conversion were performed to investigate the conversion of EBHP and its correlation to the selectivity for 1,2-epoxyoctane production. Overall, as shown in FIG. 11, there is nearly no change in the 1,2-epoxyoctane selectivity as a function of the EBHP conversion. The experiments demonstrate a clear tendency for the delaminated zeolite to be more selective than the amorphous silica catalyst, by a percentage-selectivity difference of approximately 9%. This selectivity difference demonstrates less organic hydroperoxide decomposition to alcohol and molecular oxygen (unproductive decomposition, without oxygen transfer for PO synthesis), in the zeolitic Ti-UCB-4 versus amorphous Ti—SiO$_2$ catalyst, at similar organic-hydroperoxide conversions. It is inferred that the increased selectivity must be due to the location of the Ti sites in the zeolitic catalyst. The majority of the Ti sites in Ti-UCB-4 consist of isolated framework Ti sites that are located near the external surface, in hemispherical cups, which in the fully condensed material form 12-membered ring supercages. Such confined catalytically active sites have been previously described to have a higher selectivity in ethylbenzene synthesis due to an invoked "nest effect", where two-dimensional steric confinement of reactants bound to active sites in surface pockets leads to higher reaction rates and significantly higher selectivities.

Kinetic studies for Ti-UCB-4 and Ti—SiO$_2$— Pseudo-first order rate (assuming an ideal plug-flow reactor) constants on a catalyst mass and Ti basis were calculated based on the catalysis experiments corresponding to the highest conversion for each catalyst, and results are shown in Table 2 below. On a mass of catalyst basis, the amorphous silica and crystalline Ti-UCB-4 possess similar rate constants, k' of 132 mL/(h·g cat) for Ti—SiO$_2$ and 103 mL/(h·g cat) for Ti-UCB-4. As a result of its much lower Ti content, the calculated k for Ti-UCB-4 of 25.0·10$^3$ mL/(h·g Ti) is sig- Ultraviolet-visible spectroscopy of catalysts—To characterize catalysts before and after reaction, as well as after calcination of used catalysts following reaction, diffuse-reflectance UV-Vis spectroscopy of the crystalline Ti-UCB-4 and amorphous Ti—SiO$_2$ catalysts was performed.

UV-Vis data for Ti-UCB-4 after catalysis shows a maximum at 200 nm with two shoulders, one at 210 nm and a second at 230 nm. This can be compared with a maximum of 210 nm for the fresh catalyst, which, as discussed previously, is consistent with being comprised of isolated Ti sites in the framework. The shoulder at 230 nm is interpreted as representing higher coordinated (4-coordination number) Ti sites, and it may also indicate titanium sites that are not fully condensed to the framework, i.e. containing a titanol. Upon calcining this spent catalyst, the spent/calcined Ti-UCB-4 has a maximum absorbance at 221 nm. Because framework sites have been previously attributed to be in the range of 206 nm-220 nm, it is inferred that sites in spent/calcined Ti-UCB-4 comprise isolated titanium sites in the framework, but with a shift towards titanols (Ti—OH). The color of the material after catalysis is a very pale yellow, and following calcination, it turns white.

In comparison, the absorption spectrum of the amorphous Ti—SiO$_2$ catalyst, which appears dark yellow (nearly orange) after catalysis, in contrast to the white color of the fresh catalyst. The spent catalyst shows a broad band spanning from 200 nm to 400 nm, with a maximum at 260 nm and a clear shoulder at 210 nm. Compared with the fresh Ti—SiO$_2$ catalyst, this band is much broader and has a shoulder at higher energy. Following calcination of the spent catalyst, the material appears visually white, and the breadth of this band narrows considerably in the spent/calcined Ti—SiO$_2$ catalyst, which exhibits a maximum at 260 nm and no shoulder at 210 nm. It may be inferred that the shoulder at 210 nm as well as high wavelength bands in the region above 310 nm in the spent Ti—SiO$_2$ catalyst must be due to organic residue on the catalyst surface, since these bands disappear upon calcination. The disappearance of these bands upon calcination is inconsistent with bands above 310 nm and at 21 nm in the spent Ti—SiO$_2$ catalyst as being due to aggregated Ti and isolated Ti sites, respectively, as suggested previously in the literature. In comparison, Ti-UCB-4 lacks these bands and intense coloration following catalysis—suggesting less or no organic residue poisoning sites in this catalyst.

These results further correlate the greater degree of observed stability and selectivity of the crystalline Ti-UCB-4 catalyst relative to the amorphous Ti—SiO$_2$ catalyst with the presence of organic residue forming during catalysis. It may be posited that the higher observed selectivity of the crystalline catalyst and lack of organic residue poisoning sites in this catalyst may stem from a previously observed "nest" effect. Such an effect is caused by shape selectivity of the cup in which Ti sites within Ti-UCB-4 reside, which in turn prevents organic residue, which may be polymeric in nature, from plugging up Ti sites while at the same time facilitating reaction via confinement of organic hydroperoxide and olefin reactants near the site.

In summary, this present disclosure compares a crystalline delaminated zeolite Ti-UCB-4 and an amorphous Ti—$SiO_2$ material, for the epoxidation of 1-octene with ethylbenzene hydroperoxide, under tail-end reactor conditions. While the rate constant on a mass basis is similar for both, on a Ti basis the Ti-UCB-4 significantly outperforms those of Ti—$SiO_2$. The framework sites comprising Ti-UCB-4 are also more selective and catalytically more robust, in terms of conversion versus time, when compared with amorphous Ti—$SiO_2$. Much of this difference in deactivation is correlated with poisoning by an organic residue in Ti—$SiO_2$ and the substantial lack thereof in the former.

Recyclability of catalysts—In order to investigate the possibility of activity loss of the catalysts as a result of Ti leaching, a study was conducted on the recyclability of the catalysts. Fresh and spent/calcined amorphous Ti—$SiO_2$ and crystalline Ti-UCB-4 catalysts were tested in a batch reactor system for epoxidation of 1-octene using EBHP at tail-end conditions, using the same mass of catalyst for each run as used in the flow testing. The spent catalysts correspond to a 50 h flow-catalysis experiment in which the conversion was slightly lower than the amorphous and crystalline catalysts, respectively, and after catalysis, the spent catalysts were subsequently calcined in air. Based on the results, there are no significant differences between the amorphous and crystalline material in terms of activity on a mass basis. Also, the activity is not changing for the fresh versus spent/calcined materials in this batch-reactor experiment. This shows that both amorphous and crystalline catalysts can be recycled. These results are consistent with a lack of Ti leaching in both of these catalysts result of either Ti agglomeration or leaching, as both of these would be irreversible processes (i.e. not reversed upon calcination). One interpretation of these results is that deactivation is caused by active-site blockage as a result of organic matter, which may be removed via calcination treatment. Such an interpretation is based on diffuse-reflectance UV/Ms spectroscopy of fresh, spent, and spent/calcined catalysts (vide supra).

EXAMPLE 2

The catalyst Katz-1 was synthesized by mixing 1 g of zeolite B-SSZ-70 with 1.1 g cetyltrimethylammonium bromide, 1.7 g tetrabutylammonium fluoride, 1.7 g tetrabutyl ammonium chloride, and 40 mL DMF. The mix was stirred at 100° C. for 3 days, and then sonicated for 1 h. The mix was filtered, washed with DMF, and calcined at 550° C. for 7 h. The obtained white solid was mixed with 7 mL of butanol and 0.7 mL of tetrabutoxytitanium and stirred for 1 h at 135° C. After filtration and washing with butanol, the product was dried at 120° C. The product was identified as UCB-4 via X-Ray diffraction on powder samples. Titanium incorporation was confirmed via UV-VIS spectroscopy. External surface area of the material as determined via the t-plot method was determined to be at least 100 $m^2/g$ via nitrogen physisorption, and preferably above 100 $m^2/g$ via nitrogen physisorption. This represents the catalyst of the present disclosure, which is differentiated from the prior art olefin-epoxidation catalysts, in that it is based on a crystalline framework rather than an amorphous silica network. Examples below further illustrate the utility of this crystalline framework in the performance of this catalyst under the extreme conditions corresponding to the tail end of the olefin-epoxidation flow reactor.

EXAMPLE 3

A control catalyst consisting of titanium grafted onto amorphous silica was prepared as follows: 1 g of Selecto silica gel was calcined at 550° C. for 7 h. The obtained white solid was mixed with 7 mL of butanol and 0.7 mL of tetrabutoxytitanium and stirred for 1 h at 135° C. After filtration and washing with butanol, the product was dried at 120° C. Titanium incorporation was confirmed via UV-VIS spectroscopy. External surface area of the material was determined to be ~500 $m^2/g$ via nitrogen physisorption. This catalyst serves as a control that has properties that are similar to or identical to known prior-art catalysts, which are also based on an amorphous-silica support.

EXAMPLE 4

A batch catalysis experiment was performed to simulate conditions at the tail end of an epoxidation reactor, according to available data (Ullmann's Encyclopedia of Industrial Chemistry, 2012 Wiley-VCH Verlag GmbH & Co. KGaA, Weinheim). These conditions include a reaction temperature of 130° C. and an initial chemical composition of the liquid phase that corresponds to 80% conversion of the organic hydroperoxide. Thus, a batch reactor was initially charged with 8.9 wt % 1-octene, 40.4 wt % ethylbenzene, 5.8 wt % ethylbenzene hydroperoxide, 21 wt % 1,2-epoxyoctane, 21 wt % methylphenylcarbinol, 1.5 wt % nonane. A pre-weighted amount of about 5-8 mg catalyst were added to the mixture, and the slurry was stirred at 130° C. for 4 h. After 1 h and after 4 h, separate aliquots were taken and analyzed using a gas chromatograph.

Figure 4:
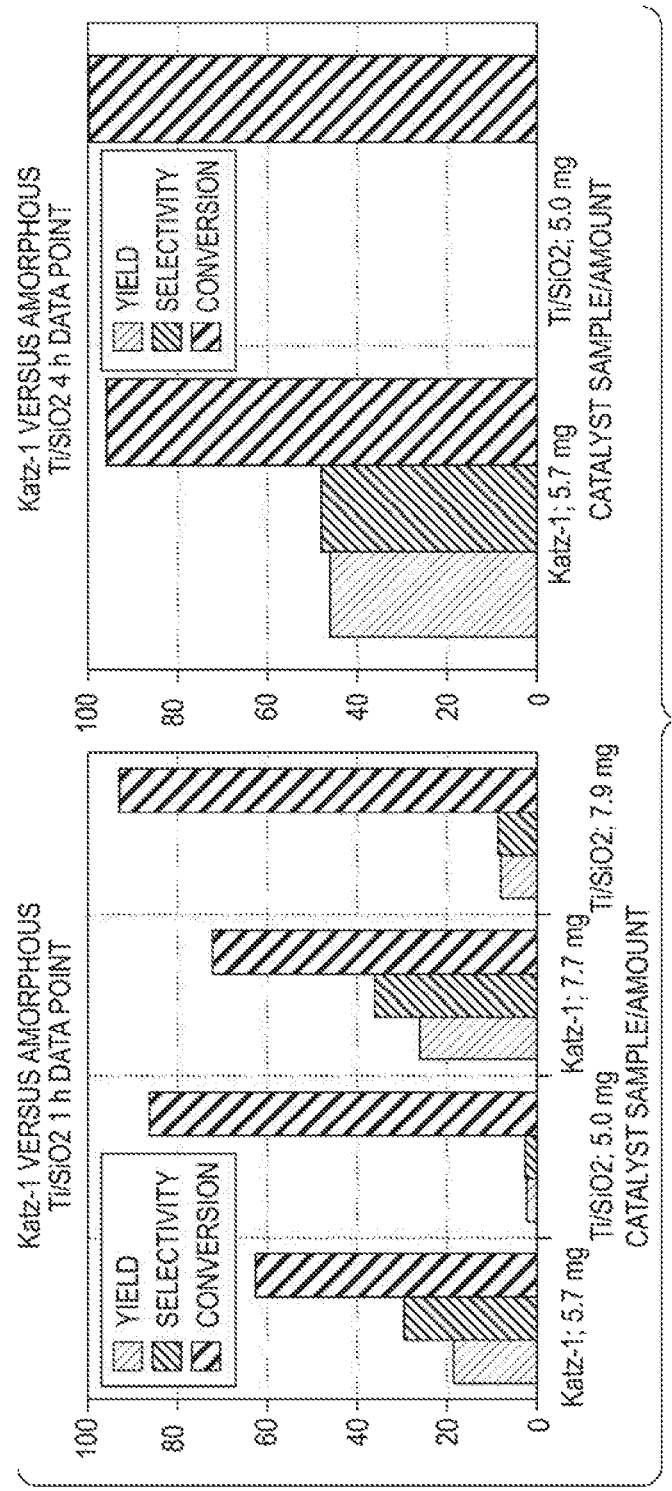
FIG. 4 illustrates example comparative charts of yield, selectivity and conversion.

A comparison of the results is illustrated in FIG. 4. FIG. 4 illustrates Yield (defined as fraction of organic hydroperoxide originally charged that has been converted to epoxide), selectivity (defined as fraction of organic hydroperoxide reacted in batch reactor that has been converted to epoxide), and conversion (defined as fraction of organic hydroperoxide originally charged that has been reacted in batch reactor) at 1 h (left panel) and 4 h (right panel) for various amounts of Katz-1 (catalyst of this invention) and Ti/$SiO_2$ (conventional catalyst) in a batch olefin-epoxidation reactor, initially charged at conditions corresponding to the tail end of the reactor.

Data in FIG. 4 (left panel) demonstrates 30.6% of the organic hydroperoxide consumed by catalyst Katz-1 after 1 h is converted to the desired epoxide product, whereas this number is 2.5% for the conventional Ti/$SiO_2$ catalyst. This is enabled by the higher selectivity of Katz-1 catalyst, which after 1 h possesses a selectivity of 30.6% versus the unselective Ti/$SiO_2$ catalyst, for which the measured selectivity after 1 h is 2.5% (selectivity is defined as fraction of organic hydroperoxide consumed that ends up as epoxide) in FIG. 4 left panel. After 4 h, 48% of the organic hydroperoxide consumed by catalyst Katz-1 is converted to the desired epoxide product, whereas this no detectable epoxide product for the conventional Ti/$SiO_2$ catalyst, based on data in FIG. 4 (right panel).

EXAMPLE 5

A catalysis experiment was performed to simulate conditions at the entrance of an epoxidation reactor. These conditions include reaction temperature of 40° C.—note the lower operating temperature relative to the tail-end-reactor operating condition in the previous example—and a chemical composition of the liquid phase simulating 0% conversion of the organic hydroperoxide. Thus, a batch reactor was charged with 35.8 wt % 1-octene, 53.4 wt % ethylbenzene 7.4 wt % ethylbenzene hydroperoxide, 2 wt % nonane, 1 wt % acetophenone, and 0.7 wt % methylphenylcarbinol. About 25 mg catalyst were added to the mix and stirred at 40° C. for 1 h. After 1 h, aliquots were taken and analyzed using a gas chromatograph.

Figure 5:
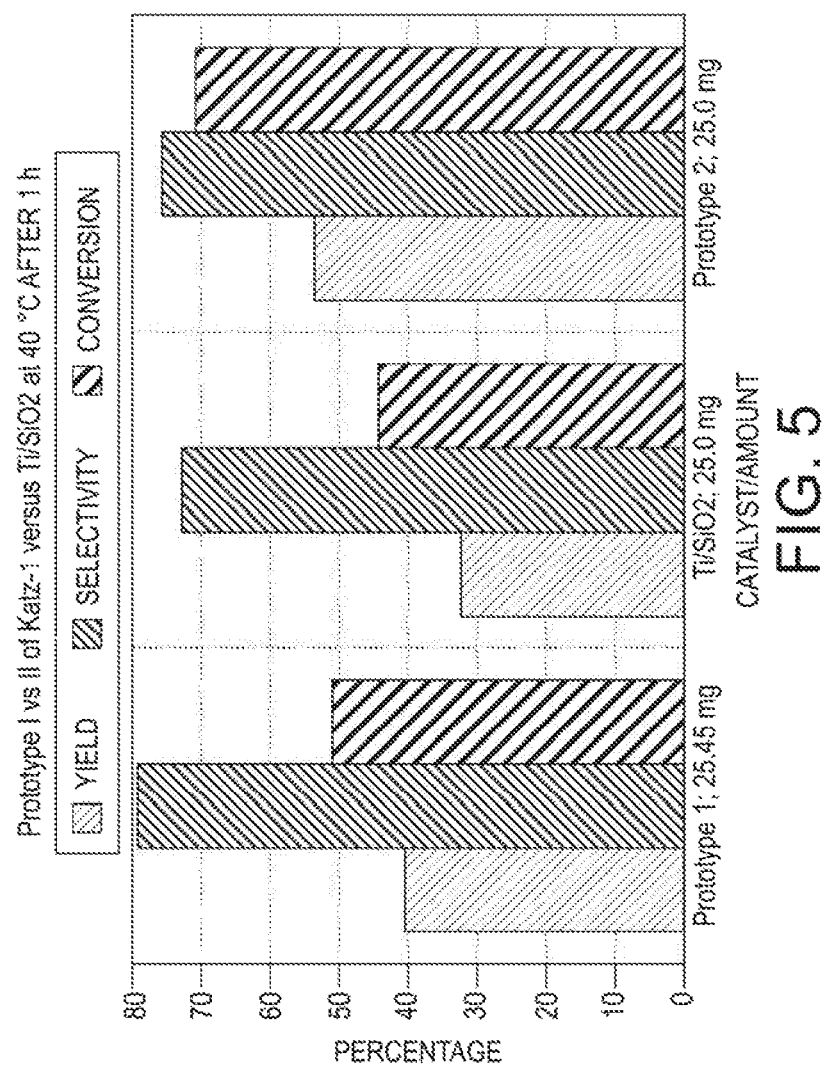
FIG. 5 illustrates second example comparative charts of yield, selectivity and conversion.

A comparison of the results is illustrated in FIG. 5. FIG. 5 illustrates Yield (defined as fraction of organic hydroperoxide originally charged that has been converted to epoxide), selectivity (defined as fraction of organic hydroperoxide reacted in batch reactor that has been converted to epoxide), and conversion (defined as fraction of organic hydroperoxide originally charged that has been reacted in batch reactor) at 1 h for Katz-1 (catalyst of this invention) and Ti/SiO$_2$ (conventional catalyst) in a batch olefin-epoxidation reactor, initially charged at conditions corresponding to the entrance of the reactor. Prototype 1 refers to catalyst Katz-1 in the figure, whereas prototype 2 refers to Katz-1 that underwent an acid treatment followed by a Ti-reinsertion treatment.

A Prototype 2 of Katz-1 (corresponding to catalyst Prototype 1 in FIG. 5) was synthesized in order to further improve the activity of Katz-1 by removing external framework titanium sites and rehydroxylation of the material in order to create more binding sites for titanium and subsequently to enable higher titanium loading. This was performed by treating 250 mg of Ti-UCB-4 with 15 mL of 2M HNO$_3$ in water at 100° C. for 1 h, followed by filtration and washing with water. After drying the sample in an oven at 120° C. in air, 1 mL Ti(BuO)$_4$ and 6 mL BuOH were added and the sample was stirred at 135° C. for 1 h, followed by filtration and washing with BuOH. Data in FIG. 5 shows that Prototype 2 is 1.7-fold more active than prototype 1, while retaining similar selectivity, at low temperature.

The data in FIG. 5 demonstrates that the catalyst of the present disclosure—Katz-1—does not offer any significant advantages compared to the conventional and known catalyst consisting of Ti/SiO$_2$ at the entrance to the reactor. The same can be concluded about Prototype 2. However, surprisingly, Katz-1 outperforms the Ti/SiO$_2$ catalyst in terms of epoxide yield and is more selective than Ti/SiO$_2$ under the conditions of FIG. 4. This means that Katz-1 is surprisingly better suited for the tail end of the reactor, not the entrance to the reactor.

EXAMPLE 6

A batch catalysis experiment was performed to simulate conditions at the tail end of an epoxidation reactor, according to available data (Ullmann's Encyclopedia of Industrial Chemistry, 2012 Wiley-VCH Verlag GmbH & Co. KGaA, Weinheim). These conditions include a reaction temperature of 110° C. and an initial chemical composition of the liquid phase that corresponds to 80% conversion of the organic hydroperoxide to methyl phenyl carbinol. Thus, a batch reactor was initially charged with 75 wt % 1-octene, 5 wt % ethylbenzene, 3 wt % ethylbenzene hydroperoxide, 15 wt % methylphenylcarbinol, 1 wt % nonane, 1 wt % acetophenone. A preweighted amount of about 25 mg catalyst were loaded in a stainless steel reactor, and the reactor was heated to 130° C. The reaction mixture was flown through the reactor at a flow rate of 6 mL/h. After 4 h, separate aliquots were taken and analyzed using a gas chromatograph.

Figure 6:
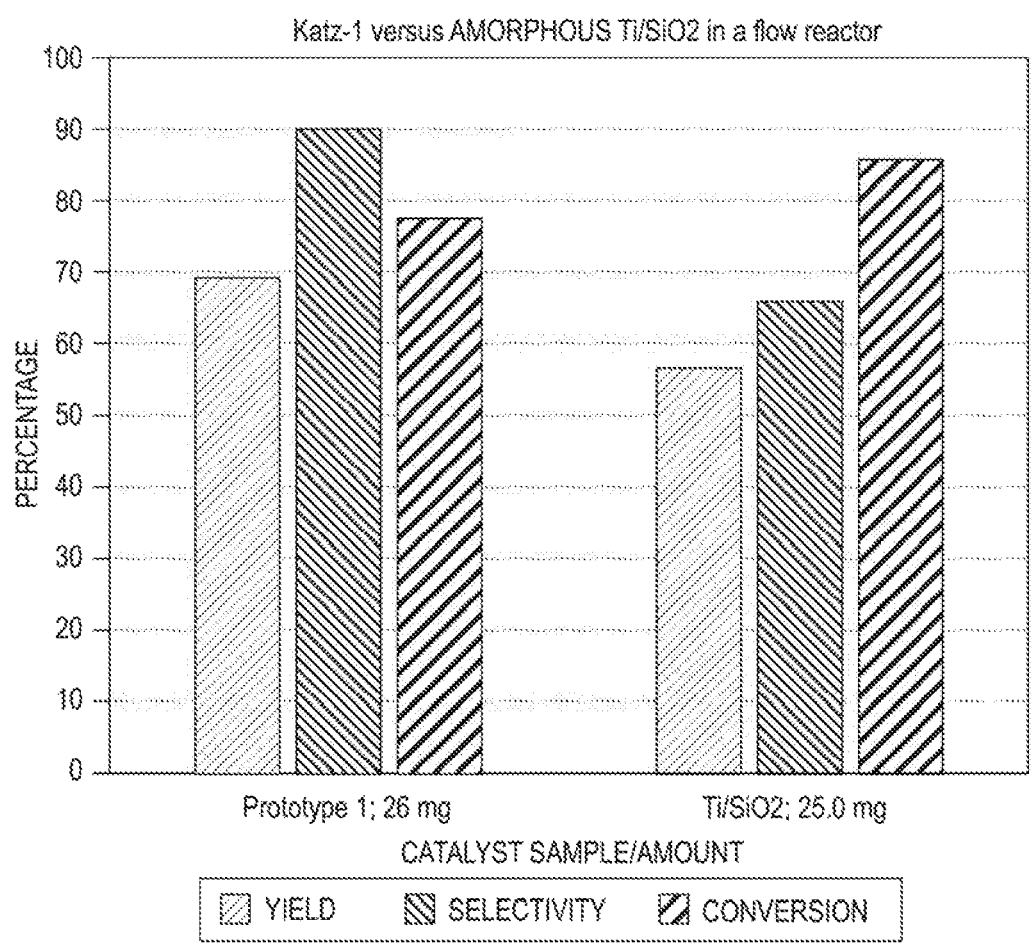
FIG. 6 illustrates third example comparative charts of yield, selectivity and conversion under flow conditions.

A comparison of the results is illustrated in FIG. 6. FIG. 6 illustrates Yield (defined as a fraction of organic hydroperoxide originally charged that has been converted to epoxide), selectivity (defined as fraction of organic hydroperoxide reacted in batch reactor that has been converted to epoxide), and conversion (defined as fraction of organic hydroperoxide originally charged that has been reacted in batch reactor) at 1 h for Katz-1 (catalyst of this invention) and Ti/SiO$_2$ (conventional catalyst) in a batch olefin-epoxidation reactor, initially charged at conditions corresponding to the entrance of the reactor.

Data in FIG. 6 demonstrates 69.4% of the organic hydroperoxide consumed by catalyst Katz-1 after 1 h is converted to the desired epoxide product, whereas this number is 56.8% for the conventional Ti/SiO$_2$ catalyst. This is enabled by the higher selectivity of Katz-1 catalyst, which after 4 h possesses a selectivity of 89.4% versus the less selective Ti/SiO$_2$ catalyst, for which the measured selectivity after 4 h is 66.1% (selectivity is defined as fraction of organic hydroperoxide consumed that ends up as epoxide) as shown in FIG. 6.

Katz-1 outperforms the Ti/SiO$_2$ catalyst in terms of epoxide yield and is more selective than Ti/SiO$_2$ under the conditions of FIG. 6. This means that Katz-1 is better suited for the tail end of the reactor.

Figure 7:
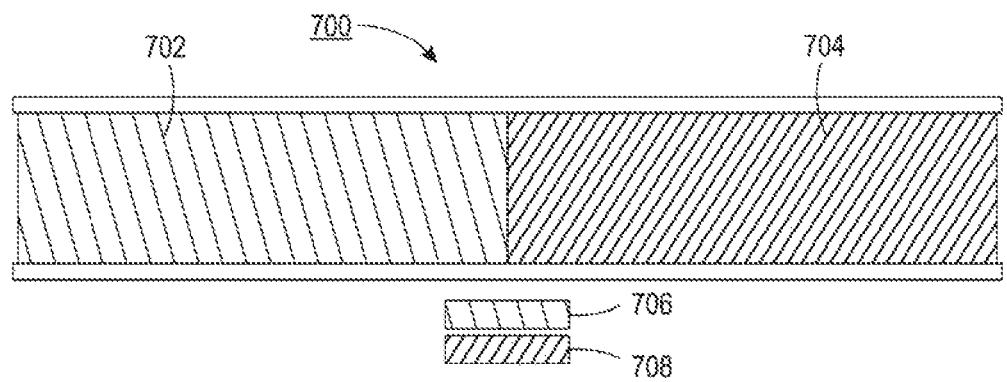
FIG. 7 illustrates an example of a first flow through reactor configuration.

The present disclosure describes different configurations that would allow Katz-1 to be utilized at the tail end of the reactor, in conjunction with one or more other catalysts being used elsewhere, at earlier conversions and residence times, in an olefin-epoxidation flow reactor. FIG. 7 schematically demonstrates a first configuration of a flow through reactor 700 that includes an entrance 702 and a tail end 704. In one embodiment, the entrance 702 may include a first solid catalyst 706 and the tail end 704 may include a second solid catalyst 708. The second solid catalyst 708 may be the preferential catalyst comprising a white crystalline solid with a titanium content of about 0.5 to about 1.5 wt %, which is based on a layered zeolite precursor that is described above. The first solid catalyst 706 and the second solid catalyst 708 may be deployed as a packed bed. In one embodiment, the flow through reactor 700 may include a region in the middle where a combination of both catalysts is used in a gradient.

Figure 8:
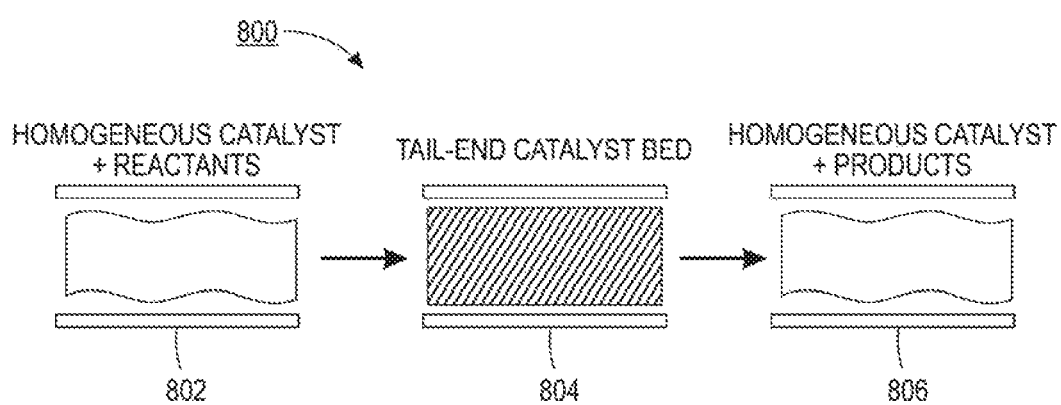
FIG. 8 illustrates an example of a second flow through reactor configuration.

FIG. 8 illustrates a second configuration of a flow through reactor 800. In one embodiment, an entrance 802 may include a dissolved homogenous catalyst and reactants (e.g., the first compound, the oxidant, the second compound, and one or more catalyst poisons, described above). In a tail end 804 of the flow-through reactor, the homogenous catalyst and the reactants may be allowed to pass through the second solid catalyst bed. Selective conversion of the oxidant may be accomplished under the extreme conditions of the tail end 804. At a section 806 after the tail end 804, the homogeneous catalyst along with product formed may exit the packed bed of the second solid catalyst in the tail end 804 of the flow-through reactor 800.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A method for converting an olefin into an epoxide, comprising:

providing the olefin in an entrance of a flow through reactor, wherein the entrance comprises a first catalyst and an oxidant, wherein the first catalyst comprises titanium grafted on an amorphous silica support or molybdenum napthenate;

converting the olefin and the oxidant into the epoxide as the olefin and the oxidant contact the first catalyst in the entrance of the flow through reactor while moving towards a tail end of the flow through reactor; and converting the olefin and the oxidant into the epoxide via a solid catalyst comprising a white crystalline solid with a titanium content of about 0.5 to about 1.5 weight percent (wt %) in the tail end of the flow through reactor.

2. The method of claim 1, wherein a temperature of the entrance of the flow through reactor is approximately 40 degrees Celsius.

3. The method of claim 1, wherein conversion of the oxidant in the tail end is greater than 80% at temperatures greater than 110 degrees Celsius.

4. The method of claim 1, wherein the oxidant comprises an organic hydroperoxide.

5. The method of claim 1, wherein the converting occurs with a residence time of at least one hour in the tail end of the flow through reactor.

* * * * *